(12) United States Patent
Ober et al.

(10) Patent No.: US 6,355,702 B1
(45) Date of Patent: Mar. 12, 2002

(54) ACYCLIC MONOMERS WHICH WHEN CURED ARE REWORKABLE THROUGH THERMAL DECOMPOSITION

(75) Inventors: Christopher K. Ober, Ithaca, NY (US); Kenji Ogino, Tokyo (JP)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/495,866

(22) Filed: Feb. 2, 2000

Related U.S. Application Data

(60) Provisional application No. 60/123,263, filed on Mar. 8, 1999.

(51) Int. Cl.$^7$ .............................. C08F 2/46; C08F 2/50; C07C 69/76
(52) U.S. Cl. .................... 522/182; 522/178; 522/49; 522/50; 522/39; 560/55; 560/96; 560/97; 560/98
(58) Field of Search .................. 522/182, 49, 50, 522/39, 178; 560/55, 96, 97, 98

(56) References Cited

U.S. PATENT DOCUMENTS

| | | | |
|---|---|---|---|
| 2,349,768 A | 5/1944 | Strain | 526/323.1 |
| 2,830,078 A | 4/1958 | Fekete | 560/221 |
| 3,201,370 A | 8/1965 | Butler et al. | 525/43 |
| 3,547,851 A | 12/1970 | Frauenglass | 524/317 |
| 3,645,984 A | 2/1972 | Dowbenko et al. | 522/89 |
| 3,647,737 A | 3/1972 | Dowbenko et al. | 526/320 |
| 4,038,475 A | 7/1977 | Frauenglass et al. | 526/323.1 |
| 4,103,081 A | 7/1978 | Repetto | 524/74 |
| 4,356,296 A | 10/1982 | Griffith et al. | 526/242 |
| 5,538,821 A | 7/1996 | Kakinoma et al. | 430/18 |

FOREIGN PATENT DOCUMENTS

EP    0422628 A2  *  4/1991

OTHER PUBLICATIONS

Chen et al. Chemical Materials. Synthesis and Characterization of Thermally Degradable Polymer Networks. 1998, 10, 3833–3838.*

Ogino, K., et al., Chem. Mater. 10, 3833–3838 (1998).

* cited by examiner

*Primary Examiner*—James J. Seidleck
*Assistant Examiner*—Sanza L McClendon

(57) ABSTRACT

Compounds containing unsaturated aliphatic moieties which are linked to each other by a tertiary oxycarbonyl containing acyclic moiety are basis for compositions which are cured to polymer networks which are thermally decomposable to provide residue which can be dissolved to allow repair of inoperative assemblies by replacement of inoperative components or recovery or recycling of operative elements which are affixed in assemblies by the cured compositions.

5 Claims, No Drawings

ACYCLIC MONOMERS WHICH WHEN CURED ARE REWORKABLE THROUGH THERMAL DECOMPOSITION

CROSS-REFERENCE TO RELATED APPLICATION

This application claims the benefit of U.S. Provisional Application No. 60/123,263, filed Mar. 8, 1999.

This invention was made at least in part with United States Government support under National Science Foundation Grant Number DMR-9321573. The United States Government has certain rights in the invention.

TECHNICAL FIELD

This invention is directed to multifunctional acyclic monomers which are cured to provide adhesives, coatings and restorative materials, and when cured, affix or coat electronic components or affix optical components, e.g., lenses and prisms, in assemblies.

BACKGROUND OF THE INVENTION

Multifunctional (meth)acrylates have been broadly used as photopolymerizable resins in a wide range of applications including adhesives, coatings, restorative materials, information storage systems and stereolithography. Highly cross-linked networks formed from these resins have desirable properties for these applications such as high strength, and very good moisture resistance and the networks are formed by rapid curing. A conventional monomer is hexane diol diacrylate (HDODA) which has the structure

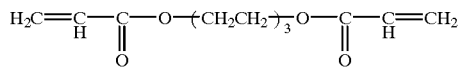

When a conventional resin is used to affix or coat an electronic component in an assembly and the assembly becomes inoperative, it is impossible to repair the assembly by replacing an inoperative component or to recover or recycle operative components of an inoperative assembly. Moreover, conventional resins are unuseful to temporarily fix components, e.g., optical components such as lenses and prisms, in an assembly. The cured resin is therefore characterized as not being reworkable, i.e., polymer network cannot readily be removed from the substrate by thermal or other treatment.

SUMMARY OF THE INVENTION

It is an object of the invention herein to provide a curable monomer which provides advantages of conventional acyclic monomers of rapid curing and cured compositions which have high strength and very good moisture resistance, and which, in addition, when cured, are reworkable through thermal decomposition.

The term "reworkable through thermal decomposition" is used herein to mean thermally degradable at a temperature of not more than 250° C. to provide decomposed product that is completely soluble in aqueous NaOH or aqueous $NH_4OH$, thereby to allow repair, replacement, recovery or recycling of components affixed or coated using the cured resin.

To this end, the invention in a first embodiment herein is directed at compounds containing unsaturated aliphatic hydrocarbon moieties which are linked to each other by a tertiary oxycarbonyl containing acyclic moiety, which when cured provide cross-linked networks which are reworkable through thermal decomposition enabling controlled and selective decomposition of the networks. These compounds may be referred to as the monomers herein.

The term "aliphatic hydrocarbon" is used herein to mean an open chain of carbon atoms which may be straight chain or branched. The term "acyclic" is used herein to define the linking moiety as not being and not containing any alicyclic, aromatic or heterocyclic group; this limitation is important since the presence of such group would increase the difficulty of decomposition. The term "tertiary oxycarbonyl" is used to mean the tertiary ester group

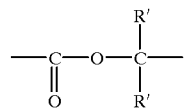

where R' is alkyl. Polymers formed from monomers with tertiary ester group are more readily decomposed than polymers from monomers with primary or secondary ester groups. The tertiary ester group is subject to breakdown into carboxylic acid and alkene at the temperatures contemplated for use for thermal degradation described hereinafter.

In a second embodiment of the invention herein there is provided a photopolymerizable composition comprising compound of the first embodiment herein and a photoinitiation effective amount of a photoinitiator.

DETAILED DESCRIPTION

The unsaturated aliphatic hydrocarbon moieties of the compounds of the first embodiment herein can be alkenyl, dienyl or alkynyl and are preferably $C_{2-10}$ alkenyl and very preferably are

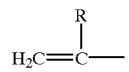

where R is hydrogen or methyl (so the compound is a diacrylate or dimethacrylate).

Preferably the tertiary oxycarbonyl moiety is

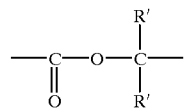

where each R' is the same or different and is $C_{1-4}$ alkyl and where each R' very preferably is methyl.

Preferably the linking moiety, i.e., the group linking the two unsaturated aliphatic hydrocarbon moieties, is

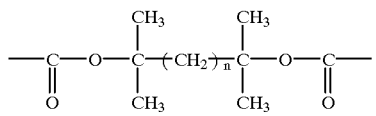

where n ranges from 1 to 30, more preferably from 1 to 6, and very preferably is 3, 4, 5 or 6. The group

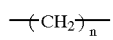

acts as a spacer between two tertiary oxycarbonyl moieties and n may be referred to as the spacer length.

Preferably the compounds of the first embodiment have the structure

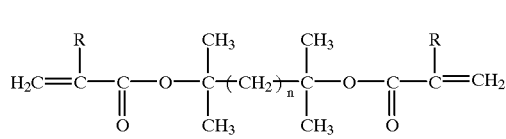

(I)

where R is hydrogen or methyl and n ranges from 1 to 30, very preferably from 1 to 6, and most preferably is 3, 4, 5 or 6. Thus, important compounds have the above structural formula where R is hydrogen and n is 4, where R is hydrogen and n is 6, where R is methyl and n is 4 and where R is methyl and n is 6. The monomers of the formula (I) are normally liquids.

The monomers of the formula (I) can be prepared according to the following reaction scheme

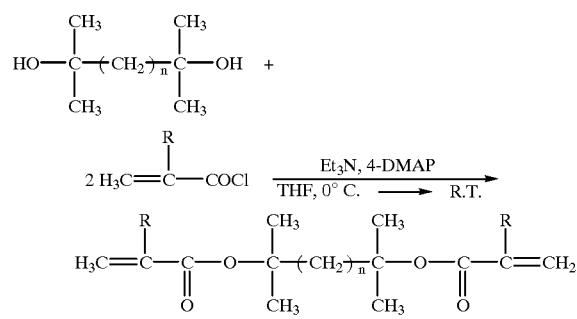

where n and R are as defined above, $Et_3N$ is triethylamine, 4-DMAP is 4-(dimethylamino)pyridine, THF is tetrahydrofuran and R.T. is room temperature. The $Et_3N$ functions as an acid acceptor. The 4-DMAP functions as a catalyst. The THF is the reaction solvent. The temperatures are used according to the following sequence: The diol, $Et_3N$ and 4-DMAP are dissolved in the THF under a nitrogen atmosphere and the solution is cooled to 0° C. Then the acryloyl chloride or methacryloyl chloride in THF is added dropwise and after a period of stirring is allowed to warm to room temperature whereupon stirring is continued. We turn now to the diol starting material. 2,5-Dimethyl-2,5-hexanediol (to provide monomer where n=2) is commercially available. The other diols can be prepared by conversion of ester groups of alkanedioic acid esters to tertiary alcohols by a Grignard reaction, e.g., by reaction of α, ω-dimethyl carboxylates, e.g., dimethyl adipate, dimethyl suberate, dimethyl sebacate, dimethyl pimelate, dimethyl azelate, or dimethyl glutarate, with methylmagnesium bromide; this reaction can be carried out by starting with a solution of carboxylate in tetrahydrofuran at 0° C., adding the methylmagnesium bromide dropwise, then allowing the reaction to warm to room temperature, stirring and recovering the diol.

We turn now to the embodiment of the invention where a curable composition is provided comprising monomer herein and a photoinitiation effective amount of a photoinitiator. These compositions are prepared by adding photoinitiator to monomer liquid, e.g., in an amount of 0.5 to 10% by weight of the monomer. A preferred photoinitiator is 2-methyl-4'-(methylthio)-2-morpholinopropiophenone which has the formula

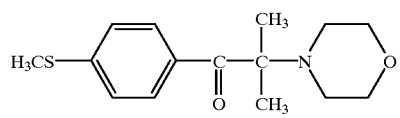

Other photoinitiators include, for example, rose bengal peroxy benzoate, substituted benzophenones and substituted hydroxy benzoins.

We turn now to the curing of the curable compositions of the second embodiment of the invention. Curing is readily carried out by exposing a film (e.g., from 50 nm to 5 mm thick, preferably from 50 nm to 0.1 mm thick) to UV light. The source of the UV light can be, e.g., a UVEXS Model 15609 (123 mW/cm$^2$) at a distance of from 0.1 to 10 cm. Other sources of UV light include, for example, mercury lamps and lasers and other conventional sources of UV light. Significantly higher rates of polymerization were observed for diacrylates than for dimethacrylates, e.g., the polymerization rate for a diacrylate was observed to be up to 20 times the polymerization rate of the corresponding dimethacrylate. The curing time is related to thickness of body of composition being cured. For a film of 0.05 mm, diacrylates cured in 30 seconds and dimethacrylates cured in 240 seconds. A correlation between spacer length and double bond conversion was observed in that the higher double bond conversions were observed for diacrylates where n is 6 or 8 compared to n being 2 or 4 and that higher double bond conversions were observed for dimethacrylates where n is 4, 6 or 8 compared to where n is 2. Where n=2, the Tg (glass transition temperature, i.e., softening point) of the polymer network was about the same for diacrylate and dimethacrylate but in the other cases of n that were observed, the Tg for polymer network diacrylates was less than that for polymer network dimethacrylates. In the case of both diacrylates and dimethacrylates, the Tg of the polymer network decreased as n increased.

Compositions to be cured in a configuration different from a film are cured by initiation of free radicals using a radical initiator. The curable compositions do not contain photoinitiator but rather a radical initiation effective amount of a radical initiator that will initiate free radicals at a temperature less than 150° C., such as benzoyl peroxide, lauryl peroxide or azobisisobutyronitrile, and curing is carried out by heating to the temperature where the initiator is functional.

We turn now to the thermal degradation of the cured compositions to residues and the dissolving of the residues. The thermal degradation is carried out by maintaining the cured composition at a temperature ranging from 155° C. to 275° C., preferably from 180° C. to 200° C., for 0.1 to 10 minutes, e.g., in a furnace or by using a directed heat probe apparatus, to decompose cured compositions to product which is entirely dissolved in aqueous ammonium hydroxide or aqueous sodium hydroxide. The decomposition provides an anhydride group which is not dissolved in water, methanol or dimethylformamide but which is subjected to ammonolysis in aqueous ammonium hydroxide or hydrolysis in aqueous sodium hydroxide. The dissolving is readily carried out by immersing the assembly where cured composition has been thermally degraded, in a body of aqueous ammonium hydroxide (e.g., 28% aqueous ammonium hydroxide solution) or aqueous sodium hydroxide (e.g., 1N sodium hydroxide solution), for example, for 0.1 to 5 minutes. A lower limit of 155° C. is selected because the cured compositions have been found to be chemically stable when maintained at temperatures up to 150° C. An upper limit of 275° C. is selected because at temperatures exceeding this, the disadvantages of degradation, crosslinking and oxidation of other parts of the assembly may occur. Decomposition rates for diacrylate networks were observed to be higher than decomposition rates for dimethacrylate networks at both 180° C. and 200° C. When the monomers had the formula (I), maximum decomposition rates (i.e., shortest time for decomposition) was observed for networks formed from monomers where n in formula (I) was 4 or 6. Polymer networks from HDODA are chemically stable at temperatures up to 370° C.

The monomers herein are uniquely useful for formulation into curable compositions to function as adhesives or coatings to temporarily hold electronic or optical components on substrates, e.g., to temporarily mount electronic components in the assembly of printed circuit boards or to temporarily fix optical components such as lenses or prisms, whereby the term of affixing may be ended by exposing the assembly to decomposing temperature in an oven and dissolving the residue. The monomers herein are also useful for formulation into curable compositions for more permanent mounting of electronic and other components, and allow repair of inoperative assemblies by replacement of inoperative components or recovering or recycling the operative components of inoperative assemblies.

The synthesis and characterization of monomers of the first embodiment herein and the synthesis and characterization of thermally degradable polymer networks are also described in Ogino, K, et al., Chem. Mater. 10, 3833–3838 (1998) which is incorporated herein by reference and in six pages where the first page is headed "Synthesis and Characterization of Reworkable Polymer Networks" which are attached as Appendix B to Provisional Application No. 60/123,263.

As indicated above, this application claims the benefit of U.S. Provisional Application No. 60/123,263; the entire disclosure of U.S. Provisional Application No. 60/123,263 is incorporated herein by reference.

The invention herein is illustrated by the following examples which are supported by the following background examples.

BACKGROUND EXAMPLE 1

Synthesis of 2,7-dimethyl-2,7-Octanediol Starting Material

To a 500-mL three-necked round-bottom flask fitted with nitrogen inlet, magnetic stirrer, dropping funnel and a condenser were added 200 mL of dry tetrahydrofuran (THF) and 17.4 g (0.1 mol) of dimethyl adipate (Aldrich) under nitrogen atmosphere. The solution was then cooled to 0° C. using an ice both. A 133 mL volume of methylmagnesium bromide solution (Aldrich, 3 M in ether, 0.4 mol) was added dropwise over 1 hour. After the addition was complete, the reaction vessel was allowed to warm to room temperature, and stirring was continued for an additional 2 hours. The reaction mixture was poured onto 350 g of crushed ice and 27 g of ammonium chloride. The upper ether layer was separated, and the aqueous layer was extracted with two 50 mL portions of ether. The combined ethereal solution was washed with dilute aqueous sodium bicarbonate and then was dried with anhydrous magnesium sulfate. After solvent evaporation, the product was crystallized from hexane/acetone (90/10). White crystalline product, 2,7-dimethyl-2, 7-octanediol was obtained (15.0 g, yield; 86%). $^1$HNMR (CDCl$_3$), δ from TMS: 1.19 [s 12H, —C(CH$_3$)$_2$OH], 1,36 [m,4H,—CH$_2$CH$_2$(CH$_3$)$_2$OH], 1.43[m, 4H, —CH$_2$CH$_2$C (CH$_3$)$_2$OH], 1.52[s, br, 2H, —OH]. IR(KBr): 3372 cm$^{-1}$ (O—H, stretch); 2971, 2938, 2862 cm$^{-1}$(C—H stretch); 1210, 1148 cm$^{-1}$(C—O—C stretch). Mp: 87° C.

BACKGROUND EXAMPLE 2

Synthesis of 2,8-Dimethyl-2,8-Nonanediol Starting Material

The synthesis was carried out as in Background Example 1 except that 18.8 g (0.1 mol) of dimethyl pimelate was substituted for the 0.1 mole of dimethyl adipate.

BACKGROUND EXAMPLE 3

Synthesis of 2,9-Dimethyl-2,9-Decanediol Starting Material

The synthesis was carried out as in Background Example 1 except that 20.2 g (0.1 mol) of dimethyl suberate was substituted for the 0.1 mole of dimethyl adipate.

BACKGROUND EXAMPLE 4

Synthesis of 2,11-Dimethyl-2,11-Dodecanediol Starting Material

The synthesis was carried out as in Background Example 1 except that 23 g (0.1 mol) of dimethyl sebacate was substituted for the 0.1 mole of dimethyl adipate.

BACKGROUND EXAMPLE 5

Synthesis of 2,6-Dimethyl-2,6-Heptanediol Starting Material

The synthesis was carried out as in Background Example 1 except that 16 g (0.1 mol) of dimethyl glutarate was substituted for the 0.1 mole of dimethyl adipate.

EXAMPLE I

Synthesis of 2,7-Dimethyl-2,7-Octanediol Diacrylate

To a 300-mL three-necked round-bottom flask fitted with nitrogen inlet, magnetic stirrer, and a dropping funnel, 8.7 g (0.05 mol) of 2,7-dimethyl-2,7-octanediol prepared as in Background Example 1, 16.7 mL (0.12 mol) of triethylamine (Fisher), 1.46 g (0.012 mol) of 4-(dimethylamino) pyridine (Aldrich), and 80 ml of dry THF were added under nitrogen atmosphere, and the solution was cooled to 0° C. The mixture of 10.8 g (0.12 mol) of distilled acryloyl chloride (Aldrich) and 20 mL of dry THF was added dropwise. After 2 hours of stirring, the reaction vessel was allowed to warm to room temperature and stirring was continued overnight. Precipitated salts were removed by filtration. A 150 mL volume of diethyl ether was added to the filtrate, and the resulting precipitate was also removed by filtration. The reaction mixture was washed with distilled water and dilute aqueous sodium bicarbonate and was dried with anhydrous magnesium sulfate. Evaporation of the solvents gave an oily residue, which was then purified by column chromatography (silica gel/hexanes). A colorless oily liquid was obtained, yield 3.2 g (23%). $^1$HNMR(CDCl$_3$), δ from TMS: 1.29 [m, 4H —CH$_2$CH$_2$C(CH$_3$)$_2$O—], 1.42 [s, 12H, —C(CH$_3$)$_2$O—], 1.74 [m, 4H, —CH$_2$CH$_2$C(CH$_3$)$_2$O—], 5.66, 6.25 [m, 4H, CH$_2$=CH—]. 5.98 [m, 2H, CH$_2$=CH—]. IR (film): 2978, 2943, 2868 cm$^{-1}$(C—H stretch); 1722 cm$^{-1}$(C=O stretch); 1636, 1620 cm$^{-1}$(C=C stretch); 1299, 1205 cm$^{-1}$(C—O—C stretch); 985 cm$^{-1}$(=CH wag); 964 cm$^{-1}$(=CH$_2$ wag); 812 c$^{-1}$ (=CH$_2$ twist).

EXAMPLE II

Synthesis of 2,7-Dimethyl-2,7-Octanediol Dimethacrylate

Synthesis was carried out as in Example I except that 12.5 g (0.12 mol) of distilled methacryloyl chloride was substituted for the acryloyl chloride.

EXAMPLE III

Synthesis of 2,8-Dimethyl-2,8-Nonanediol Diacrylate

Synthesis was carried out as in Example I except that 9.4 g (0.05 mol) of 2,8-dimethyl-2,8-nonanediol prepared as in Background Example 2 was substituted for the 2,7-dimethyl-2,7-octane diol.

EXAMPLE IV

Synthesis of 2,8-Dimethyl-2,8-Nonanediol Dimethacrylate

Synthesis was carried out as in Example III except that 12.5 g (0.12 mol) of distilled methacryloyl chloride was substituted for the acryloyl chloride.

EXAMPLE V

Synthesis of 2,9-Dimethyl-2,9-Decanediol Diacrylate

Synthesis was carried out as in Example I except that 10.1 g (0.05 mol) of 2,9-dimethyl-2,9-decanediol prepared as in Background Example 3 was substituted for the 2,7-dimethyl-2,7-octanediol.

EXAMPLE VI

Synthesis of 2,9-Dimethyl-2,9Decanediol Dimethacrylate

Synthesis was carried out as in Example V except that 12.5 g (0.12 mol) of distilled methacryloyl chloride was substituted for the acryloyl chloride.

EXAMPLE VII

Synthesis of 2,11-Dimethyl-2,11-Dodecanediol Diacrylate

Synthesis was carried out as in Example I except that 23 g (0.05 mol) of 2,11-dimethyl-2,11-dodecanol prepared as in Background Example 4 was substituted for the 2,7-dimethyl-2,7-octane diol.

EXAMPLE VIII

Synthesis of 2,11-Dimethyl-2,11-Dodecanediol Dimethacrylate

Synthesis was carried and as in Example VII except that 12.5 g (0.12 mol) of distilled methacryloyl chloride was substituted for the acryloyl chloride.

EXAMPLE IX

Synthesis of 2,5-Dimethyl-2,5-Hexanediol Diacrylate

Synthesis was carried out as in Example I except that 14.5 g (0.5 mol) 2,5-dimethyl-2,5-hexanediol (purchased from Aldrich) was substituted for the 2,7-dimethyl-2,7-octane diol.

EXAMPLE X

Synthesis of 2,5-Dimethyl-2,5-Hexanediol Dimethacrylate

Synthesis was carried out as in Example IX except that 12.5 g (0.12 mol) of distilled methacryloyl chloride was substituted for the acryloyl chloride.

EXAMPLE XI

Synthesis of 2,6-Dimethyl-2,6-Heptanediol Diacrylate

Synthesis was carried out as in Example I except that 16 g (0.05 mol) of 2,6-dimethyl-2,6-heptanediol prepared as in Background Example 5 was substituted for the 2,7-dimethyl-2,7-octane diol.

EXAMPLE XII

Synthesis of 2,6-Dimethyl-2,6-Heptanediol Dimethacrylate

Synthesis was carried out as in Example XI except that 12.5 g (0.12 mol) of distilled methacryloyl chloride was substituted for the acryloyl chloride.

EXAMPLE XIII

Preparing Curable Compositions and Curing

For each of the monomers synthesized in Examples I, II and V–X, curable composition was made by adding 1 wt% of 2-methyl-4'-(methylthio)-2-morpholinopropiophenone to the liquid monomer. In each case, a drop of curable composition was placed on a glass slide and squeezed into a film of about 0.05 mm thickness using a cover glass. Photopolymerizations were carried out by exposing the films to UV light generated from a UVEXS 15605 (123 mW/cm$^2$). The distance between the light source and the monomer film was 5 cm. UV irradiation time was 30 seconds for diacrylates and 240 seconds for dimethacrylates. Double bond conversions were monitored by FT-IR (Mattson 2020 Galaxy series FT-IR spectrometer). Glass transition temperatures, Tg, were measured according to dynamic mechanical analysis procedure described in Ogino K, et al., Chem. Mater. 10, 3833–3838 (1998) which is Appendix A hereto. The results are set forth in Table 1 below wherein DA stands for diacrylate, DMA stands for dimethacrylate and n refers to formula I and n=2 (DA) is for cured monomer of Example IX, n=2 (DMA) is for cured monomer of Example X, n=4 (DA) is for cured monomer of Example I, n=4 (DMA) is for cured monomer of Example II, n=6 (DA) is for cured monomer of Example V, n=6 (DMA) is for cured monomer of Example VI, n=8 (DA) is for cured monomer of Example VII, and n=8 (DMA) is for cured monomer of Example VIII.

TABLE 1

| Double-Bond Conversion (%) | | | $T_g$ (° C.) | |
| --- | --- | --- | --- | --- |
| n | DA | DMA | DA | DMA |
| 2 | 90 | 90 | 180 | 185 |
| 4 | 91 | 86 | 150 | 165 |
| 6 | 96 | 85 | 85 | 140 |
| 8 | 97 | 86 | 55 | 135 |

The results show a correlation between spacer length and double bond conversion in that higher double bond conversions were observed for diacrylates where n is 6 or 8 compared to n being 2 or 4 and that higher double bond conversions were observed for dimethacrylates where n is 4, 6 or 8 compared to where n is 2. The results show furthermore that the Tg of the polymer network was about the same for diacrylates and dimethacrylates when n is 2, but in the other cases of n, the Tg of the polymer network diacrylates were less than for dimethacrylates, and that in the case of both diacrylates and dimethacrylates, the Tg of the polymer network decreased as n increased.

EXAMPLE XIV

Thermal Degradation and Dissolving of Decomposed Product

The thermal decomposition behavior was investigated with a DuPont 951 Thermogravimetric Analyzer (TGA) under nitrogen flow. Samples were prepared for decomposition by curing between glass slides using a 0.5 mm Teflon spacer. Isothermal TGA measurements were carried out at 150, 180 and 200° C. over 200 minutes of thermal treatment at 150 and 180° C. and over 60 minutes at 200° C. The thermogravimetric analyzer measured weight loss. The cured compositions investigated were cured monomers of Examples I, II and V through X and also cured conventional 1,6-hexanediol diacrylate (HDODA). At 150° C., no significant weight loss was observed after a 180 minute thermal treatment for all networks examined. The results for the monomers of Examples I, II and V through X at 180° C. and 200° C. are shown in Table 2 below where the same shorthand is used as in Example XIII and maximum rates are given in %/minute and the values in parentheses represent the time in minutes when the maximum rate was observed.

TABLE 2

| | 180° C. | | 200° C. | |
| --- | --- | --- | --- | --- |
| n | DA | DMA | DA | DMA |
| 2 | 1.1 (90) | 0.7 (140) | 4.0 (21) | 3.7 (27) |
| 4 | 2.1 (65) | 1.0 (80) | 7.8 (16) | 3.9 (18) |
| 6 | 2.5 (65) | 1.2 (85) | 9.5 (16) | 4.2 (24) |
| 8 | 1.5 (125) | 0.8 (130) | 7.0 (20) | 3.5 (29) |

As shown in Table 2, diacrylate networks took less time to reach the maximum weight loss rate compared with dimethacrylate networks at 180° C. and 200° C. When the number of ethylene units (n) was equal to 4 or 6, the shortest time to reach maximum weight loss was the case for both diacrylate networks and dimethacrylate networks. No weight loss was observed for polymer network from HDODA when maintained at 200° C. for 60 minutes which was selected as being representative of much longer times than 60 minutes. Polymer network from HDODA started to lose weight only at temperatures above 370° C. After decomposition, the solubility of residual product was assessed by immersion in water, methanol, and dimethylformamide, i.e., DMF, the usual solvents for poly (acrylic acid) and poly(methacrylic acid), and also in 1N sodium hydroxide solution, and aqueous ammonium hydroxide (28%). Decomposition products were readily soluble in sodium hydroxide solution and in aqueous ammonia indicating networks did fully decompose and were reworkable. These decomposition products were not soluble in water, methanol and DMF. Decomposition products of HDODA and HDODMA (decomposed above 370° C.) were not soluble in aqueous NaOH and $NH_4OH$.

Variations

Many variations of the above will be obvious to those skilled in the art. Thus, the invention is defined by the claims.

What is claimed is:

1. A compound having the structural formula:

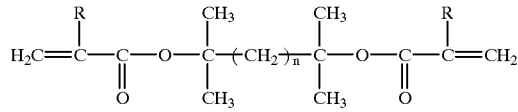

where R is selected from the group consisting of hydrogen and methyl and n is 4, 5 or 6.

2. A compound according to claim 1 where n in the structural formula is 3, 4, 5 or 6, and where R in the structural formula is hydrogen.

3. A compound according to claim 1 where n in the structural formula is 4, 5 or 6, and where R in the structural formula is methyl.

4. Curable composition comprising a compound containing unsaturated aliphatic hydrocarbon moieties which are linked to each other by a tertiary oxycarbonyl containing acyclic moiety and a photoinitiation effective amount of a photoinitiator, which, when cured, provides cross-linked networks that are re-workable through thermal decomposition.

5. The composition of claim 4 where the photoinitiator is 2-methyl-4'-(methylthio)-2-morpholinopropiophenone.

\* \* \* \* \*